United States Patent
Cremer

[19]

[11] Patent Number: 6,083,533
[45] Date of Patent: Jul. 4, 2000

[54] LAYERED TABLET FOR THE CONTROLLED RELEASE OF ACTIVE SUBSTANCES

[75] Inventor: Karsten Cremer, Bonn, Germany

[73] Assignee: LTS Lohmann Therapie-Systeme GmbH, Neuwied, Germany

[21] Appl. No.: 08/983,278

[22] PCT Filed: Jun. 24, 1996

[86] PCT No.: PCT/EP96/02736

§ 371 Date: Jan. 7, 1998

§ 102(e) Date: Jan. 7, 1998

[87] PCT Pub. No.: WO97/02812

PCT Pub. Date: Jan. 30, 1997

[30] Foreign Application Priority Data

Jul. 7, 1995 [DE] Germany .......................... 195 24 753

[51] Int. Cl.⁷ ................. A61K 9/24; A61K 9/26
[52] U.S. Cl. .................. 424/472; 424/468; 424/469; 424/470
[58] Field of Search ..................... 424/472, 468, 424/469, 473, 470

[56] References Cited

U.S. PATENT DOCUMENTS

| | | | |
|---|---|---|---|
| 4,786,507 | 11/1988 | Schmidt | 424/472 |
| 4,966,772 | 10/1990 | Ohm et al. | 424/482 |
| 5,279,832 | 1/1994 | Greissinger et al. | 424/438 |
| 5,549,913 | 8/1996 | Colombo et al. | 424/472 |

*Primary Examiner*—James M. Spear
*Attorney, Agent, or Firm*—Wenderoth, Lind & Ponack, LLP.

[57] ABSTRACT

A layered tablet for the controlled release of active substances in a liquid medium comprising at least one active substance-containing, layered matrix with contact surfaces to the liquid medium which are at least partially provided with a cover layer delaying or preventing the active substance release, is characterized by the fact that the cover layer is at least one additional layer lying with thickness gradients on contact surfaces of the layered, prefabricated matrix, or that the matrix is at least one additional layer lying with thickness gradients on contact surfaces of the layered, prefabricated cover layer, which additional layer is applied by pressing powdery or granular material on the layered, prefabricated matrix or on the layered, prefabricated cover layer.

8 Claims, 2 Drawing Sheets

LAYERED TABLET FOR THE CONTROLLED RELEASE OF ACTIVE SUBSTANCES

This application is a 371 of PCT EP96/02736 filed Jun. 24, 1996.

The present invention relates to a layered tablet for the controlled release of active substances in a liquid medium, which comprises at least one active substance-containing layered matrix having contact surfaces to the liquid medium, its contact surfaces being provided, at least partially, with a cover layer delaying or preventing the active substance release. Said layered tablet is characterized by the fact that the cover layer is a layer lying with thickness gradients on contact surfaces of the layered matrix, and which is applied on the layered matrix by means of pressing on powdery or granular material which is erodable in the liquid medium. The present invention in particular relates to a layered tablet for the controlled release of pharmaceutical active substances in the fluids of the gastrointestinal tract or in liquids suitable to test drugs.

BACKGROUND OF THE INVENTION

In the art of pharmaceutical technology layered tablets are tablets consisting of several, firmly adhering, parallel or concentrically curved layers of compressed powder or granulate particles (cf. Hunnius Pharmazeutisches Wörterbuch, 6th edition, Berlin 1986). In contrast to press-coated tablets, which are defined as tablets with a preformed core having a material completely surrounding the core and formed by compressing a powder or granular material, conventional layered tablets are manufactured in one operation and in a tablet press by repeatedly compressing different kinds of particles, the layers obtaining a characteristic form owing to the fact that the same press is used in each compression. For this reason, the forms of the individual layers cannot be chosen freely, i.e., independently of each other. The use of biplanar punches results in layered tablets having consistently parallel layers, except for the border areas in the region of the optional facet. If curved punches are used, the lower layer, which is pressed first, assumes a biconvex shape, whereas the upper or second layer has a uniform thickness and is parallel with the curved upper boundary surface of the layer pressed first.

In 1917, layered tablets and a process for their production were described for the first time (U.S. Pat. No. 1,248,571). They are used in pharmacy for several considerations. On the one hand, they offer the possibility of combining incompatible active substances in one tablet in a spatially separated form. On the other hand, they permit combination of several formulations having different release properties. For instance, the one layer may be used to release an initial dose of the active substance in the form of a fast-disintegrating, quick-releasing formulation, whereas the second layer comprises a maintenance dose in retarded form.

Quite recently, special layered tablets for the controlled release of active substances, in particular for zero-order release, have been described (U. Conte et al., J. Controlled Rel. 26, pp. 39–47, 1993). These layered tablets comprise an active substance-containing swelling matrix and at least one excipient ingredient layer pressed thereon and covering the matrix surface on one side. The layer of inactive ingredients is substantially inert and impermeable to active substances. The active substance-containing matrix releases the active substance in liquid media by means of diffusion.

Swelling of the matrix in aqueous medium is intended to ensure that the release rate does not decrease in the course of substance release—owing to progressive active substance depletion of the matrix and simultaneous extension of the diffusion path, but is maintained in terms of a zero-order process. This swelling causes a substantial enlargement of the matrix surface as compared to its dry state. However, the published data relating to the actual release behavior of these layered tablets show that the swelling effect in most practical cases is not sufficient to maintain the initial release rate. If, on the other hand, the swelling matrix is formulated such that it swells in an aqueous medium to an extreme extent, insufficient cohesion of the tablet is nearly inevitable: it disintegrates and thereby results in "dose dumping", i.e., a sudden release of the remaining active substance.

In administration forms other than layered tablets, the design principle of continuously enlarging a matrix' contact surface to the liquid release medium to control the release rate has been realized in a different manner. WO 94/0747 describes, at least basically, the use of an envelope having a thickness differing at several sites and consisting of a material which is erodable in a liquid medium; this envelope is designed for devices belonging to the type of coated solid drugs (coated tablets and capsules) produced by conventional coating or film-coating methods. During the release of active substance, the envelope erodes; this process is terminated at the thinnest sites of the envelope first, and it proceeds in a continuous or discontinuous manner. The superficial expansion of the envelope decreases, whereas the contact surface of the core to the release medium increases.

WO 94/0747 describes tablets covered with a coating. However, it does not show a possible selective production of the thickness gradients of the coating which are required to utilize the effect of boundary enlargement. The conventional coating methods, which are mentioned as production method, inevitably result in slightly non-uniform thicknesses with certain core shapes. For example, when tablets or capsules are coated, it cannot be prevented that the film thickness is below average at the edges and at sites having a small radius of curvature. In examples 1 and 4, the conventional coating methods are not even varied to obtain a non-uniform thickness. Moreover, it is not to be expected that these coating methods (fluidized bed and coating pan methods are mentioned) can be performed such that the thickness gradients of the erodable envelope, which are necessary for a continuous surface enlargement of the core, can be formed in a selective manner.

In view of the lack of suitable manufacturing methods for such administration forms with erodable coatings having thickness gradients, there is a need of alternative solutions which are no longer based on the design principle comprising a core and a coating. German patent application P 43 41 442.7 already teaches, although mainly with reference to the Figures, that thickness gradients to obtain the above-mentioned effect can also be realized by arranging the administration form in approximately parallel layers; however, there are no indications with respect to a preferred embodiment, for example, in the form of a coextruded article or several pressed pieces which are glued together. If pressed articles are used for the active substance-containing matrix or for the erodable excipient layer, there is no useful indication with respect to production engineering, except for the fact that an adhesion-promoting auxiliary material should be used, if the layers do not adhere to each other by themselves, i.e., which kind of suitable production method or design of device should be used to allow an efficient combination or joining of the pressed pieces to form an administration form, as in the case of a layered tablet, for example.

BRIEF SUMMARY OF THE INVENTION

It is accordingly the object of the present invention to provide a layered tablet for the controlled release of active substances comprising a layered, active substance-containing matrix, which layered tablet can easily be manufactured with known tablet presses and whose cover layer controls the release rate of active substance in a liquid medium, but which does not exhibit the mentioned disadvantages of the art.

This object is achieved in a layered tablet for the controlled release of active substances in a liquid medium comprising at least one active substance-containing, layered matrix having contact surfaces to the liquid medium, its contact surfaces being provided, at least partially, with a cover layer delaying or preventing the active substance release, with the present invention by forming the layered tablet in that the cover layer is at least on additional layer lying with thickness gradients on contact surfaces of the layered, prefabricated matrix, or that the matrix is at least one additional layer lying with thickness gradients on contact surfaces of the layered, prefabricated cover layer, which additional layer is applied by pressing powdery or granular material on the layered, prefabricated matrix or on the layered, prefabricated cover layer.

DETAILED DESCRIPTION OF THE INVENTION

A layered tablet according to the present invention belongs to the group of layered tablets which have an active substance-containing, layered matrix and a cover layer lying on said matrix and controlling the active substance release. In contrast to the layered tablets of this group known in the art, the cover layer is at least one layer lying on with thickness gradients and applied by pressing on a powdery or granular material which is erodable in liquid media.

The solution according to the present invention applies the principle of controlling the release rate by erosion of a cover layer's material, wherein said erosion is controlled by thickness gradients, to the class of layered tablets. The release rate of active substances in such a layered tablet is controlled by its geometric shape, in particular by the thickness gradients of the cover layer and its erosion rate.

At the beginning of release, the active substance diffuses from the edge region of the active substance-containing matrix layer into the surrounding release medium. The cover layer represents a diffusion barrier first.

As the release proceeds the border regions of the active substance-containing matrix-layer become poor in active substance. Longer diffusion paths to the contact surface with the release medium and reduced concentration gradients at the contact surface have an unfavorable effect on the release rate. At the same time, however, there is a compensatory effect. The cover layer erodes, enlarging the available contact area to the release medium.

If the thickness gradients are chosen appropriately, these two opposing influences on the release rate can therefore be adjusted, resulting in a zero-order kinetics which is often desirable in therapy.

However, the thickness gradients may also be chosen in a different way, for example, such that a substantial enlargement of the contact surface between active substance-containing matrix and release medium is effected only at the end of the release process.

Most advantageously, a layered tablet according to the present invention may also be formed such that powder or granular material to form a cover layer controlling the active substance release is compressed on both sides of the active substance-containing matrix layer. This results in a three-layer tablet whose outward appearance differs from conventional three-layer tablets, in particular, by the selectively incorporated thickness gradients of the layers. In this case, the controlling influence of the cover layers on the release rate is even greater than that of only one cover layer, since there is a larger potential increase in contact area between matrix layer and liquid medium.

If the layered tablet is to comprise two or more active substances to be released in a controlled manner, it may be advantageous or necessary to also provide the active substance-containing matrix with more than one layer. This enables a release at predetermined rates even with active substances diffusing through the matrix layers at different rates. In this connection differing release rates, whether for one or for more active substances, may be realized. For instance, one active substance quantity may be released relatively quickly in terms of an initial dose, and another active substance amount may be released in a retarded manner in terms of a maintenance dose, from different active substance-containing matrix layers.

It is favorable for production to coordinate the geometry of the active substance-containing matrix layer and that of the cover layer such that both layers have thickness gradients whose directions complement each other. Such a construction allows a conventional biplanar or biconvex overall form of the layered tablet. On the one hand, the layered tablet can thus be processed on all standard machines for further processing (coating, finishing, etc.) or testing; on the other hand, it is possible to predetermine the thickness gradients by the form of the matrix layer. Since this is pressed first, for which purpose very simple tablet presses may be used, conventional, relatively unproblematic compression molds may be used in the following, extremely more critical step when the cover layer is pressed on by means of special presses.

Assuming a biconvex overall geometry, the layered tablet according to the present invention may certainly also be provided with a polymer film or a sugar-containing coat in a subsequent coating procedure. In this manner, ill-smelling or evil-tasting active substances can be masked, tablets marked, enteric coatings produced, and other usual objects in tablet coating can be realized.

According to the invention, the combination of the following steps is designed as production method for a layered tablet according to the present invention. At first, an active substance-containing matrix layer is manufactured on a conventional eccentric or rotary press, preferably using a special punch formed such that already the resulting pressed piece is provided with thickness gradients being complementary to the desired thickness gradients of the following cover layer. In addition to different punches, the use of special tableting machines is required for compression with the powdery or granular material for the cover layer. These special machines must be capable of receiving the pressed piece and inserting it precisely into a die opening which can then be filled with the material for the cover layer, and both components can be compressed. Presses for layered tablets are not capable of performing this; however, special coated tablet compressing machines of a new generation have been offered for some time now. They have transfer elements under vacuum to receive pressed articles and to transfer them into die orifices. These machines are particularly suitable for the production of the layered tablets according to the present invention because of the precision with which they can receive and move the prefabricated pressed articles.

In principle the production may also be carried out in reversed order; the cover layer is manufactured in the form of a pressed piece first, followed by compressing it under addition of the powder or granular material for the active substance-containing matrix layer.

Combining the layered tablet with other components can make the layered tablet according to the present invention another drug with other administration forms. Of particular advantage is the combination with a therapeutic system having a prolonged action in the stomach. A controlled active substance release over a period that is even longer than that of existing depot forms can be achieved thereby, since the residence time in the absorptive section of the gastrointestinal tract is increased.

An advantageous embodiment of the layered tablet may be present by the fact that the matrix consists of more than one layer, and that each of said layers is of a different material and/or comprises different active substances.

The matrix itself may be erodable or non-erodable in the liquid medium; in the latter case the active substance is released by diffusion.

If the matrix erodes, its erosion must be slower than that of the cover layer.

Moreover, an active substance-containing matrix may have thickness gradients whose direction is complementary to the cover layer lying thereon. In addition, the layered tablet according to the present invention may have two active substance-containing matrices whose contact surfaces to the liquid release medium have different cover layers, wherein these are provided with different thickness gradients and may consist of differently erodable materials. The thickness gradients of both the active substance-containing matrix layer and/or the cover layer may vary over the extent thereof either continuously or discontinuously.

BRIEF DESCRIPTION OF THE DRAWING

In the following the present invention will be illustrated in greater detail by means of embodiment examples shown in the accompanying drawings, wherein:

FIG. 1 a shows a so-called coated tablet with a preformed core (10) and a shell (11) completely surrounding it and also formed by compressing powder or granular material. The core (10) and/or the shell (11) may comprise different active substances. If the shell (11) is free of active substances, it may be a delayed-action form of a press-coated tablet; for example, the material of the shell (11) erodes in differently acidic or alkaline environment of the gastrointestinal tract, followed by active substance release from the core (10) in different regions of the intestinal tract.

Figure 1A:
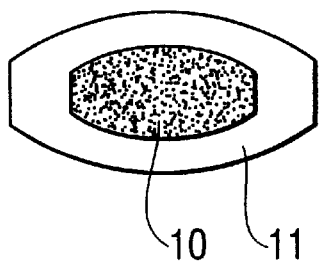
FIGS. 1a, 1b, 1c: show typical layered tablets from:
  a) Hunnius Pharmazeutisches Wörterbuch
  b) and c) Pharmaceutical Dosage Forms, Vol. 1 (ed. H. A. Lieberman et al)
Figure 1B:
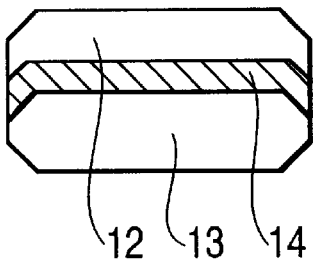
Figure 1C:
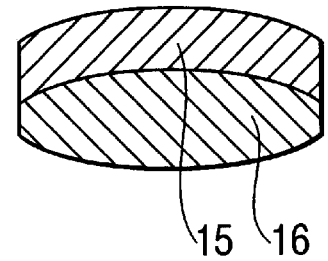

The layers (12 to 14) of the layered tablet 1b may be applied in similar manner, and the same applies to the layers (15, 16) of the tablet according to FIG. 1c.

Figure 2:
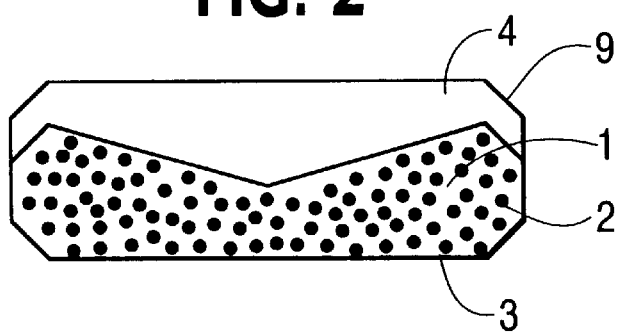
FIGS. 2 to 5: show different embodiments of layered tablets according to the present invention or of parts thereof.

FIG. 2 shows an example of a layered tablet according to the present invention. It is a biplanar tablet form with facet edge (9). The layered tablet has a layered matrix (1) comprising active substance (2) and a surface (3) representing in a liquid medium the contact area between the active substance-containing matrix and the medium. Part of the surface or contact area (3) is provided with a cover layer (4) pressed on the layered matrix (1) and delaying or preventing the active substance release, it consists of erodable material with thickness gradients.

Figure 3:
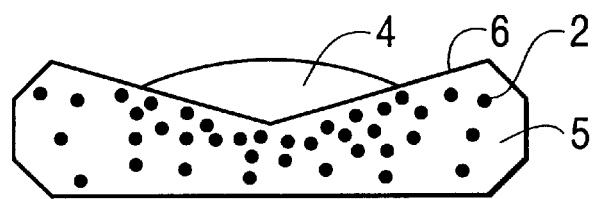

FIG. 3 shows the state of the layered tablet according to the present invention of FIG. 2 in the course of release. The border regions (5) of the layered active substance-containing matrix (1) which are not covered by the cover layer (4) have released part of the active substance (2); they have become poor in active substance. At the sites of small thickness the erosion of the cover layer (4) has already created additional contact surface (6) at the layered matrix.

Figure 4:
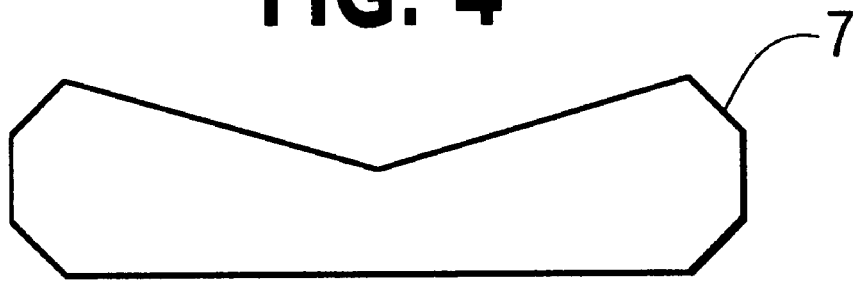

FIG. 4 exemplifies a possible state after completed active substance release; the release-delaying cover has completely eroded from the layered matrix (7) which is now free of active substance.

Figure 5:
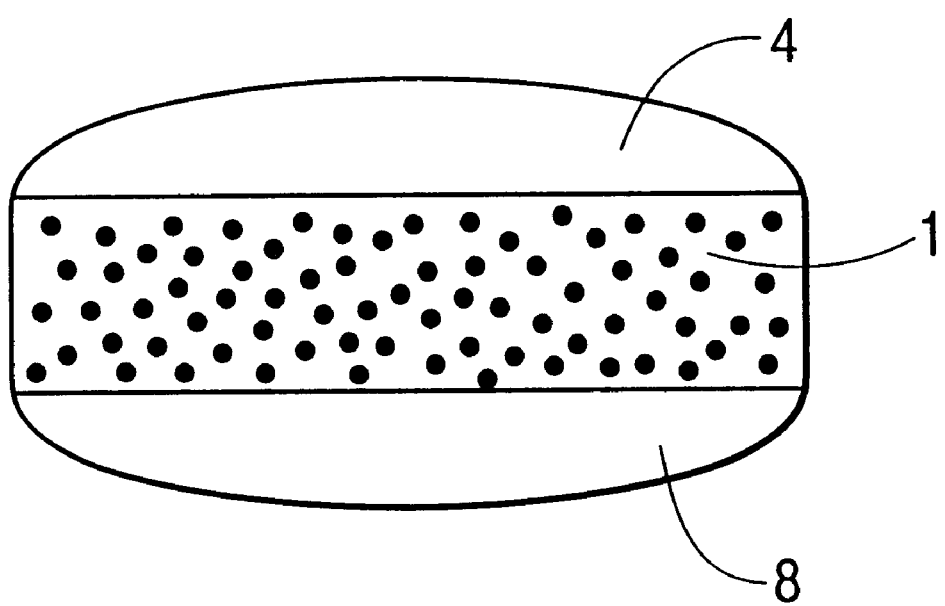

FIG. 5 shows another embodiment of a layered tablet according to the present invention. This is a biconvex three-layer tablet having a biplanar, active substance-containing matrix layer (1) and two cover layers (4 and 8) of erodable material pressed thereon.

What is claimed is:

1. A process for producing a layered tablet for the controlled release of at least one active substance in a liquid, said tablet comprising at least one active substance-containing layered matrix having an active substance releasing surface when contacting the liquid medium, said releasing surface being provided, at least partially, with a cover layer which delays or prevents the active substance release wherein:

a) the active substance-containing layer matrix is a formed body which is prestressed, has thickness gradients and is formed from a powder or granulate of an active substance-containing substrate,
   b) the cover layer is an additional layer which has thickness gradients and is formed from a powder or granulate of a substrate, which is erodible in the liquid medium, by pressing the cover layer onto the releasing surface of the matrix, and
   c) the thickness gradients of the cover layer controlling the active substance release rate are predetermined by the shape of the matrix layer, the direction of the thickness gradient of the matrix being complementary to the direction of the thickness gradients of the cover layer, wherein said process comprises:
   1) inserting the active substance-containing matrix layer in the form of a prefabricated pressed piece into a die of a tableting machine, and
   2) compressing the prefabricated pressed piece into a layered tablet under the addition of a powder or granular material for the cover layer.

2. The process according to claim 1, wherein a rotary tablet press with vacuum-transfer elements is used to insert the prefabricated matrix layer piece into the die.

3. The process of producing a layered tablet according to claim 1, wherein the cover layer consists of more than one layer.

4. The process of producing a layered tablet according to claim 1, wherein the active substance containing matrix contains more than one layer, and each layer is of a different material and/or comprises different active substances.

5. A process for producing a layered tablet for the controlled release of at least one active substance in a liquid, said tablet comprising at least one active substance-containing layered matrix having an active substance releasing surface when contacting the liquid medium, said releasing surface being provided, at least partially, with a cover layer which delays or prevents the active substance release wherein:

a) the active substance-containing layer matrix is a formed body which is prestressed, has thickness gradients and is formed from a powder or granulate of an active substance-containing substrate, b) the cover layer is an additional layer which has thickness gradients and is formed from a powder or granulate of a substrate, which is erodible in the liquid medium, by pressing the cover layer onto the releasing surface of the matrix, and c) the thickness gradients of the cover layer controlling the active substance release rate are predetermined by the shape of the matrix layer, the direction of the thickness gradient of the matrix being complementary to the direction of the thickness gradients of the cover layer, wherein said process comprises 1) inserting the cover layer in the form of a prefabricated pressed piece into a die of a tableting machine, and 2) compressing said prefabricated piece into a layered tablet under the addition of a powder or granular material for the active substance-containing matrix layer.

6. The process according to claim 5, wherein a rotary tablet press with vacuum-transfer elements is used to insert the prefabricated cover layer piece into the die.

7. The process of producing a layered tablet according to claim 5, wherein the cover layer consists of more than one layer.

8. The process of producing a layered tablet according to claim 5, wherein the active substance containing matrix contains more than one layer, and each layer is of a different material and/or comprises different active substances.

* * * * *